US008754660B2

(12) United States Patent
Kandori et al.

(10) Patent No.: US 8,754,660 B2
(45) Date of Patent: Jun. 17, 2014

(54) CAPACITIVE DETECTION TYPE ELECTRO-MECHANICAL TRANSDUCER

(75) Inventors: Atsushi Kandori, Ebina (JP); Makoto Takagi, Kawasaki (JP); Masao Majima, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 505 days.

(21) Appl. No.: 12/973,733

(22) Filed: Dec. 20, 2010

(65) Prior Publication Data

US 2011/0169510 A1 Jul. 14, 2011

(30) Foreign Application Priority Data

Jan. 12, 2010 (JP) ................................. 2010-003649

(51) Int. Cl.
*G01R 27/26* (2006.01)
*G01D 5/24* (2006.01)
(52) U.S. Cl.
CPC ............ *G01R 27/2605* (2013.01); *G01R 27/26* (2013.01); *G01D 5/24* (2013.01)
USPC .......................................... 324/686; 324/661
(58) Field of Classification Search
USPC .................................................. 324/686, 661
See application file for complete search history.

(56) References Cited

U.S. PATENT DOCUMENTS

| 5,144,466 | A | 9/1992 | Nakamura et al. ............. 359/123 |
|---|---|---|---|
| 5,343,314 | A | 8/1994 | Nakamura et al. ............. 359/123 |
| 5,396,360 | A | 3/1995 | Majima ......................... 359/133 |
| 5,586,131 | A | 12/1996 | Ono et al. ....................... 372/19 |
| 5,659,560 | A | 8/1997 | Ouchi et al. ..................... 372/27 |
| 5,801,861 | A | 9/1998 | Majima ......................... 359/124 |
| 5,998,924 | A | 12/1999 | Yamamoto et al. ............ 313/496 |
| 6,430,109 | B1* | 8/2002 | Khuri-Yakub et al. ........ 367/181 |
| 6,759,888 | B1 | 7/2004 | Wodnicki ....................... 327/382 |
| 7,149,442 | B2 | 12/2006 | Ushijima et al. ................ 399/48 |
| 7,382,137 | B2 | 6/2008 | Ushijima et al. .............. 324/458 |
| 7,741,851 | B2 | 6/2010 | Ushijima et al. .............. 324/458 |
| 7,802,476 | B2* | 9/2010 | Lasalandra et al. ......... 73/514.32 |
| 2008/0264167 | A1 | 10/2008 | Kandori et al. ............. 73/504.12 |
| 2008/0294050 | A1 | 11/2008 | Shinomura et al. ........... 600/459 |
| 2009/0164051 | A1* | 6/2009 | Vervoordeldonk ........... 700/302 |
| 2009/0193893 | A1 | 8/2009 | Kandori et al. ............. 73/504.12 |

(Continued)

OTHER PUBLICATIONS

S. Manohar, et al., "The Twente Photoacoustic Mammoscope: system overview and performance," Phys. Med. Biol. 50 (2005).

(Continued)

*Primary Examiner* — Jeff Natalini
(74) *Attorney, Agent, or Firm* — Fitzpatrick, Cella, Harper & Scinto

(57) ABSTRACT

A capacitive detection type electro-mechanical transducer comprises; a cell formed by a first electrode arranged on a substrate and a second electrode arranged on a vibration film, and a detection circuit for detecting a displacement of the vibration film, based on a capacity change between the first and second electrodes, wherein a plurality of the cells are classified into a plurality of groups, each one includes at least two cells, and the first electrodes or the second electrodes of the cells of the same one group are commonly connected to the same one detection circuit, and an addition circuit for adding, into single information, signals from the plurality of detection circuits corresponding to the plurality of groups, and for outputting the information, and a capacitive load for each one of the detectors are formulated to be dispersedly arranged.

7 Claims, 3 Drawing Sheets

(56) References Cited

U.S. PATENT DOCUMENTS

| | | | |
|---|---|---|---|
| 2009/0205423 A1 | 8/2009 | Takagi et al. | 73/504.14 |
| 2010/0141355 A1* | 6/2010 | Kharrat et al. | 333/197 |
| 2010/0213791 A1 | 8/2010 | Kandori et al. | 310/309 |
| 2011/0031568 A1 | 2/2011 | Kandori et al. | 257/419 |

OTHER PUBLICATIONS

A.S. Ergun, et al., "Capacitive Micromachined Ultrasonic Transducers: Fabrication Technology," IEEE Transactions on Ultrasonics, Ferroelectrics, and Frequency Control vol. 52, No. 12, (Dec. 2005).

* cited by examiner

CAPACITIVE DETECTION TYPE ELECTRO-MECHANICAL TRANSDUCER

BACKGROUND OF THE INVENTION

1. Field of the Invention

The present invention relates to a capacitive detection type electro-mechanical transducer, and specifically relates to a capacitive detection type electro-mechanical transducer that can be employed for, e.g., a capacitive detection type ultrasonic sensor.

2. Description of the Related Art

There are known diagnostic apparatuses for breast tumors, which apply the photoacoustic effect.

For example, in order to detect ultrasonic waves from an object, a PVDF sensor (approximately 75 mm square) including a total of 590 pixels arranged with a pitch of approximately 3 mm, each pixel having a width of 2 mm is used. PVDF sensors have a wider bandwidth compared to PZT sensors.

As with PVDF sensors, capacitive detection type ultrasonic sensors (CMUTs: Capacitive Micromachined Ultrasonic Transducers) using a MEMS technique have been proposed as sensors having a wider bandwidth compared to PZT sensors (A. S. Ergun, Y. Huang, X. Zhuang, O. Oralkan, G. G. Yaralioglu, and B. T. Khuri-Yakub, "Capacitive micromachined ultrasonic transducers: fabrication technology", IEEE Transactions on Ultrasonics, Ferroelectrics, and Frequency Control, Vol. 52, No. 12, p.p. 2242-2258, December 2005).

CMUTs can be formed at low cost because they are formed by applying a semiconductor process. For CMUTs, a pixel pitch of 250 to 400 μm is used depending on the frequency band of the object to be measured.

It can be expected that use of a CMUT in a breast tumor diagnostic apparatus applying the photoacoustic effect brings cost reduction in the sensor part of the apparatus.

However, as a result of diligent study, the present inventors found that if the pixel size of a CMUT is simply increased (i.e., the number of cells (or elements) included in one pixel is increased), the following problems arise.

A CMUT, which is an electrostatic capacitive detection type sensor, includes a detection circuit that detects a current change caused by a capacitance change.

If a pixel size employed for a conventional CMUT is increased to a size for a breast tumor diagnostic apparatus, a larger capacitance load will be put on each pixel in the CMUT. Thus, a larger load will be put on each detection circuit, causing a problem in requiring the detection bandwidth to be narrowed in order for the detection circuit to stably operate.

In view of the above problem, an object of the present invention is to provide a capacitive detection type electro-mechanical transducer enabling expansion of a frequency bandwidth for each detection circuit to stably operate, and thus, enabling provision of a wide detection bandwidth even where the size of each pixel is increased.

SUMMARY OF THE INVENTION

A capacitive detection type electro-mechanical transducer according to the present invention comprises a cell formed by a first electrode arranged on a substrate and a second electrode arranged on a vibration film in opposition to the first electrode to form a gap between the first and second electrodes; and a detection circuit for detecting a displacement of the vibration film, based on a capacity change between the first and second electrodes, wherein a plurality of the cells are provided, and a plurality of detection circuits are provided, the plurality of cells are classified into a plurality of groups, each one includes at least two cells, and the first electrodes or the second electrodes of the cells of the same one group are commonly connected to the same one detection circuit, and an addition circuit for adding, into single information, signals from the plurality of detection circuits corresponding to the plurality of groups, and for outputting the information, and a capacitive load for each one of the detectors are formulated to be dispersedly arranged.

The present invention achieves a capacitive detection type electro-mechanical transducer enabling expansion of a frequency bandwidth for each detection circuit to stably operate, and thus, achieves a wide detection bandwidth even where the size of each pixel is increased.

Further features of the present invention will become apparent from the following description of exemplary embodiments with reference to the attached drawings.

DESCRIPTION OF THE EMBODIMENTS

Figure 1:
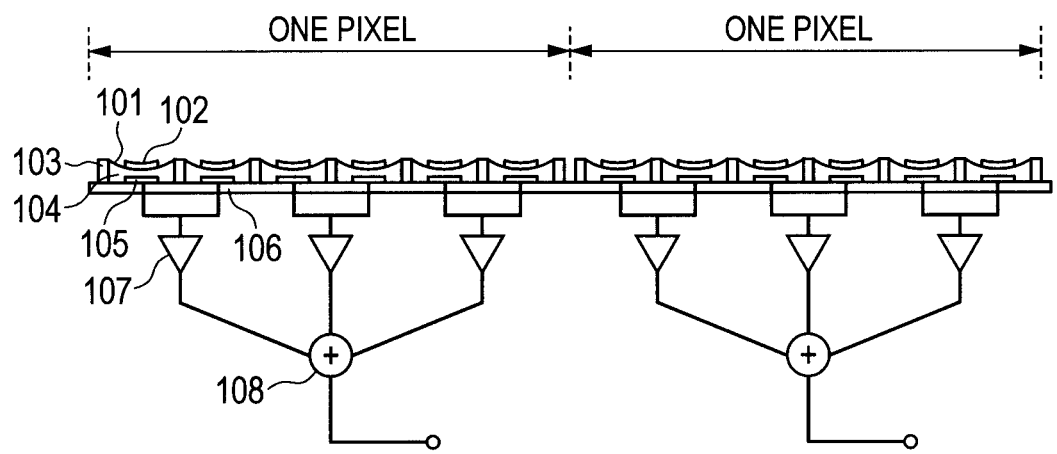
FIG. 1 is a diagram illustrating a capacitive detection type electro-mechanical transducer according to a first embodiment.

Preferred embodiments of the present invention will now be described in detail in accordance with the accompanying drawings.

Hereinafter, an example of a configuration of a capacitive detection type electro-mechanical transducer according to each of embodiments of the present invention, which is capable of detecting a displacement of a vibration film based on a capacitance change between a first electrode (detection electrode) and a second electrode (bias electrode) will be described with reference to the drawings. In the present invention, the first electrode and the second electrode may be arranged with a gap therebetween. For the functions of the respective electrodes, the first electrode may be a bias electrode while the second electrode being a detection electrode. In other words, in the present invention, either the first electrode or the second electrode may be used as a detection electrode.

First Embodiment

A CMUT forming a capacitive detection type electro-mechanical transducer according to a first embodiment will be described with reference to FIG. 1.

In the CMUT according to the present embodiment, one pixel refers to an area in which ultrasonic wave information received by a vibration film 101 is output as one piece of averaged information.

In one pixel 1, amplitude and phase information for ultrasonic waves is averaged, and the relevant apparatus forms an image of an object based on the pixel-based amplitude and phase information.

The vibration film 101 is supported by a supporting portion 103 formed on a substrate 106. Each of the vibration film 101, the supporting portion 103 and the substrate 106 includes an insulating material.

The CMUT according to the present embodiment includes detection electrodes (first electrodes) 105 arranged on the substrate 106, and bias electrodes (second electrodes) 102 arranged on the vibration films 101 via the detection electrodes 105 and gaps 104 so as to face the detection electrodes 105.

A configuration set including a detection electrode arranged on a substrate and a bias electrode arranged on a vibration film via the detection electrode and a gap so as to face the detection electrode is referred to as a "cell".

A constant DC voltage is applied to each bias electrode 102. The pressure of each gap 104 portion is reduced by the pressure of the atmosphere.

Each vibration film 101 bends to the substrate 106 side owing to an electrostatic force generated by the difference in potential between the bias electrode 102 to which a bias voltage has been applied and the detection electrode 105, and the difference between the pressure of the atmosphere applied to the upper portion of the vibration film 101 and the pressure of the gap 104 portion.

Upon the vibration film 101 vibrating according to ultrasonic waves, an electrostatic capacitance between the bias electrode and the detection electrode changes according to the vibration.

The electrostatic capacitance change and the bias voltage applied to the bias electrode cause the detection electrode 105 to generate an inductive charge, resulting in a weak current flowing in the detection electrode 105.

The CMUT according to the present embodiment includes a plurality of cells in each pixel.

The size (thickness and diameter) of a vibration film in each cell is determined so that the vibration film can easily vibrate at the frequencies of detection-target ultrasonic waves. The size of each pixel is determined by the wavelengths of detection-target ultrasonic waves.

In general, the cell has a diameter in a range of around ten to several tens of micrometers, and as mentioned in the Description of the Related Art section above, each pixel has a size of around 2 mm in a breast tumor diagnostic apparatus applying the photoacoustic effect.

Therefore, each pixel includes a plurality of (around 100 to 4000 in the above example) cells.

In the CMUT according to the present embodiment, the cells in each pixel are divided into N groups.

More specifically, each pixel includes a plurality of groups, each including detection electrodes (first electrodes) 105 interconnected via a wiring and further connected to a same detection circuit 107.

Although FIG. 1 illustrates an example in which the electrodes 105 arranged on the substrate 106 are used for the first electrodes, which are detection electrodes, in the present invention, the first electrodes 105 and the second electrodes 102, which are bias electrodes, may be interchanged to use the second electrodes for the detection electrodes. In this case, each pixel may include a plurality of groups, each including detection electrodes (second electrodes) 102 interconnected via a wiring and further connected to a same detection circuit 107.

The CMUT according to the present invention includes one detection circuit for each of N groups (N detection circuits in total) in each pixel.

Consequently, a capacitance load imposed on each detection circuit can be dispersed, enabling expansion of a frequency bandwidth for detection signals in which the detection circuit stably operates, and thus, enabling provision of a CMUT that can provide a wide bandwidth to a breast tumor diagnostic apparatus applying the photoacoustic effect without narrowing the detection bandwidth even though the pixel size is increased.

The CMUT according to the present embodiment includes one addition circuit 108 for each pixel.

Each addition circuit 108 adds up all the output signals from the N detection circuits included in the relevant pixel and outputs a signal resulting from the addition to an output signal terminal of the CMUT.

Provision of an addition circuit 108 for each pixel enables reduction of the number of wirings drawn to the outside of the CMUT.

Consequently, downsizing and reliability enhancement of the CMUT can be achieved. Also, a load on an apparatus that receives signals from the CMUT can be reduced.

Second Embodiment

A CMUT forming a capacitive detection type electro-mechanical transducer according to a second embodiment will be described with reference to FIG. 2.

Figure 2:
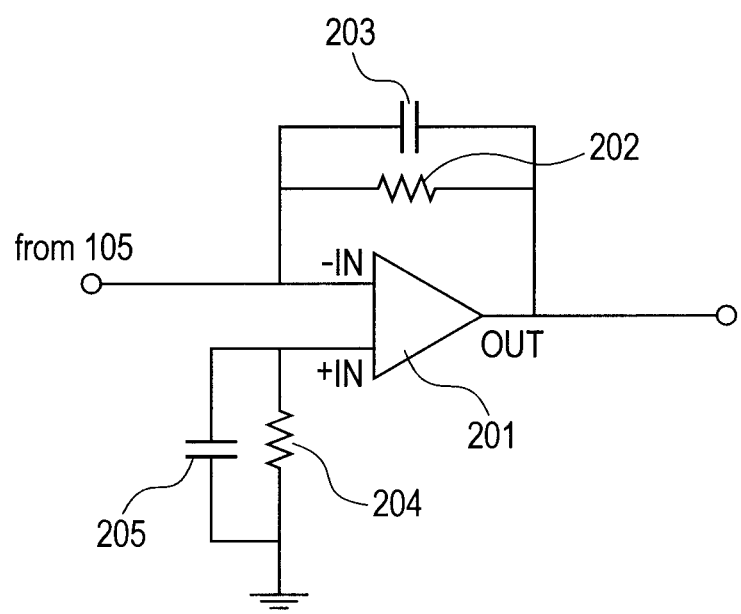
FIG. 2 is a diagram illustrating a capacitive detection type electro-mechanical transducer according to a second embodiment.

FIG. 2 is a diagram of a configuration of a trans-impedance circuit.

The configuration in FIG. 2 includes an operational amplifier 201, resistances 202 and 204 and capacitors 203 and 205. Components corresponding to those in FIG. 1 will be described with reference to FIG. 1.

The present embodiment is the same as the first embodiment except the configuration of each detection circuit and the division count related thereto. Here, a detection circuit 107 is a circuit for detecting a weak current generated by vibration of a vibration film.

In the present embodiment, a trans-impedance circuit, which is a current-to-voltage conversion circuit that converts a change in a weak current into a voltage, is used.

In FIG. 2, the operational amplifier 201 is connected to positive and negative power supplies VDD and VSS.

An inverting input terminal (−IN) of the operational amplifier 201 is connected to a wiring from a detection electrode 105 in the CMUT.

An output terminal (OUT) of the operational amplifier 201 is connected to the inverting input terminal (−IN) via the resistance 202 and the capacitor 203 connected in parallel, forming a configuration in which an output signal is fed back.

A non-inverting input terminal (+IN) of the operational amplifier 201 is connected to a ground terminal (GND) via the resistance 204 and the capacitor 205 connected in parallel.

The voltage of the ground terminal (GND) has an intermediate potential between the positive power supply VDD and the negative power supply VSS.

The resistances 202 and 204 has a same resistance value and the capacitors 203 and 205 have a same capacitance value.

Each detection circuit 107 according to the present embodiment converts changes in currents from corresponding detection electrodes 105 into a voltage value according to the current changes by means of a trans-impedance circuit and outputs the voltage value.

The trans-impedance circuit has a wide bandwidth compared to other circuit configurations.

Furthermore, since an output signal from the detection circuit 107 takes the form of a voltage value, signal degradation is less likely to occur in a wiring connected to an addition circuit.

Each addition circuit 108 is a voltage addition circuit, which adds up output voltages from corresponding detection circuits 107 and outputs the resulting voltage from an output terminal to the outside.

Here, it is assumed that a gain bandwidth of the operational amplifier 201 is GBW, the resistance values of the resistances 202 and 204 are RF, the capacitance values of the capacitors are CF, and a capacitance parasitic in the non-inverting input terminal (+IN) of the operational amplifier is Cin.

When an operational amplifier is made to perform a trans-impedance operation in the trans-impedance circuit illustrated in FIG. 2, it is necessary to consider the stability of the overall circuit because an input signal is subjected to a negative feedback via RF and CF. Where the capacitance Cin parasitic in the input terminal is large, the negative feedback circuit becomes unstable, which may result in the circuit itself oscillating. When the circuit has entered such state, the circuit cannot perform current-to-voltage conversion that it should perform, and thus, it is necessary to select optimum GBW, RF and CF considering the circuit stability for the value of Cin.

When the input terminal has the parasitic capacitance Cin, it is necessary to satisfy expression (1) in order for the operational amplifier to stably operate.

$$Cin \leq \pi \times GBW \times R_F \times (C_F)^2 \qquad \text{Expression (1)}$$

It is assumed that a capacitance parasitic in the detection electrode 105 portions is Cmut for one pixel in the CMUT. It is also assumed that a parasitic capacitance is Cwiring for one wiring connected from the detection electrodes 105 to the detection circuit 107. Furthermore, it is assumed that a division count for one pixel, that is, the number of groups in which detection electrodes are connected (the number of detection circuits) is an integer N.

The parasitic capacitance Cin of the input terminal can be expressed by expression (2) using the capacitance Cmut parasitic in the detection electrode 105 portions and the capacitance Cwiring parasitic in the connection wiring, and the division count N for one pixel.

$$Cin = \frac{Cmut}{N} + Cwire \qquad \text{Expression (2)}$$

Expression (3) can be derived from expressions (1) and (2).

$$N \geq \frac{Cmut}{\pi \times GBW \times R_F \times (C_F)^2 - Cwire} \qquad \text{Expression (3)}$$

Determining the division count N so as to satisfy expression (3) enables a stable circuit operation even using a predetermined constant for the trans-impedance circuit.

In the CMUT according to the present embodiment, the division count N for one pixel is determined using expression (3).

As described above, the division count N and the detection circuit count can be determined in relation to the gain bandwidth of an operational amplifier, the parasitic capacitance generated in the detection electrodes forming the detection electrodes for one piece of information, and the parasitic capacitance between the detection electrodes and the corresponding detection circuit, based on the predetermined gain bandwidth, the feedback capacitance and the resistance value of the trans-impedance circuit.

Consequently, with detection circuits, the number of which is set to N, even where the pixel size is increased, the detection circuits can be made to stably operate for a wide bandwidth.

Third Embodiment

A CMUT forming a capacitive detection type electro-mechanical transducer according to a third embodiment will be described with reference to FIG. 3.

The present embodiment is the same as the first and second embodiments except the configurations of detection circuits and addition circuits.

Figure 3:
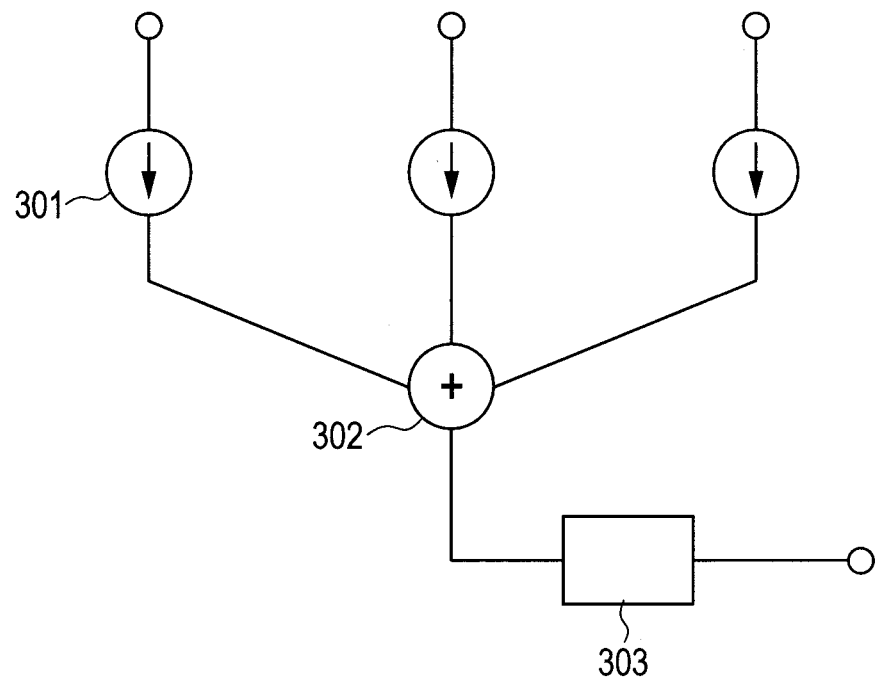
FIG. 3 is a diagram illustrating a capacitive detection type electro-mechanical transducer according to a third embodiment.

The configuration illustrated in FIG. 3 includes current amplification circuits 301, a current addition circuit 302 and a current-to-voltage conversion circuit 303. Detection circuits 107 are formed by the current amplification circuits 301.

Also, an addition circuit 108 is formed by the current addition circuit 302 and the current-to-voltage conversion circuit 303.

Each current amplification circuit 301 amplifies a weak current from the corresponding detection circuit 107, performs impedance conversion and outputs the resulting current to the addition circuit 108.

In the addition circuit 108, a plurality of input currents are added up by means of the current addition circuit 302.

A current resulting from the addition is converted into a corresponding voltage signal in the current-to-voltage conversion circuit, and output to the outside of the CMUT.

The current amplification circuits 301 and the current addition circuit 302 can be provided in a smaller circuit area compared to the trans-impedance circuit and the voltage addition circuit used in the first embodiment. Accordingly, the areas of the detection circuit 107 and the addition circuit 108 can be decreased.

Use of the CMUT according to the present embodiment enables provision of a CMUT with a smaller circuit area without narrowing the detection bandwidth even where the pixel size is increased.

Fourth Embodiment

A CMUT forming a capacitive detection type electro-mechanical transducer according to a fourth embodiment will be described with reference to FIG. 4.

The present embodiment is the same as the first to third embodiments excepts the configuration of substrates on which detection circuits and addition circuits are formed.

Figure 4:
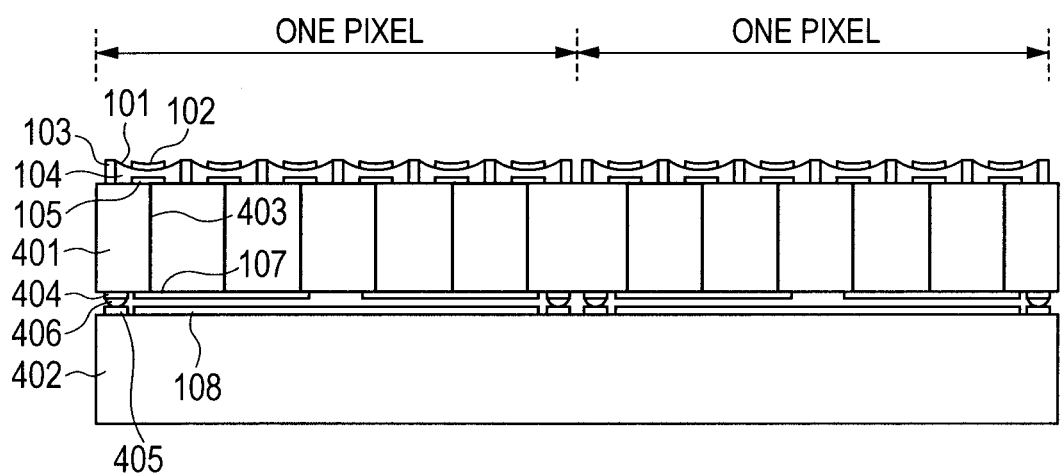
FIG. 4 is a diagram illustrating a capacitive detection type electro-mechanical transducer according to a fourth embodiment.

FIG. 4 is a diagram illustrating a configuration of the CMUT according to the present embodiment.

The configuration illustrated in FIG. 4 includes a first substrate 401, a second substrate 402, penetrating wirings 403, detection circuit output terminals 404, addition circuit input terminals 405 and bumps 406.

On a surface of the first substrate 401, cells in a plurality of groups are arranged with the respective detection electrode sides (first electrode sides) of the cells facing the surface.

In other words, on one surface of the substrate, pixels, each including cells that each includes a detection electrode 105, are formed.

Also, on another surface of the substrate (surface opposite the surface on which the cells in the plurality of groups are provided), respective detection circuits in the plurality of groups are formed. In other words, N detection circuits 107 are formed for each pixel.

The first substrate 401 includes a number of wirings penetrating the substrate, the number corresponding to a pixel count P multiplied by the cell count for one pixel, and detection electrodes for each group are connected to a corresponding detection circuit (P×N detection circuits in the entire CMUT) via the corresponding penetrating wirings.

On the second substrate 402, a number of addition circuits, the number corresponding to the pixel count P, are formed.

Output terminals of the detection circuits formed on the first substrate 401 and input terminals 405 of the addition circuits formed on the second substrate are electrically connected by pixel via bumps.

Output signals from the CMUT are drawn out to a number of terminals formed on the second substrate 402, the number corresponding to the pixel count P, via a number of wirings, the number corresponding to the pixel count.

Using the CMUT according to the present embodiment, the length of each wiring from pixels can be suppressed to around the thickness of the first substrate 401, enables reduction of parasitic capacitances generated by the wirings.

Accordingly, a wide bandwidth CMUT with a further decreased load on the detection circuits.

Fifth Embodiment

Figure 5:
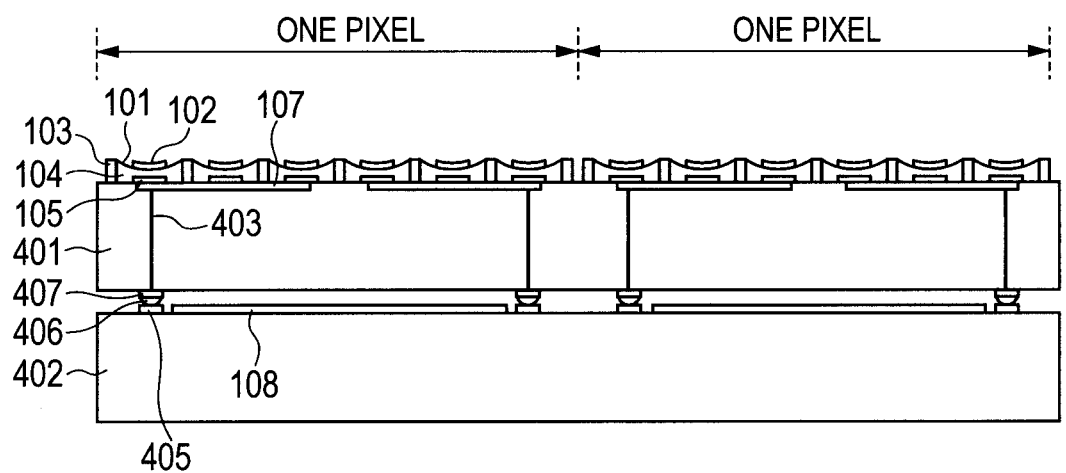
FIG. 5 is a diagram illustrating a capacitive detection type electro-mechanical transducer according to a fifth embodiment.

A CMUT forming a capacitive detection type electro-mechanical transducer according to a fifth embodiment will be described with reference to FIG. 5.

The present embodiment is the same as the fourth embodiment except the positions on a substrate where detection circuits are formed.

On a first substrate 401, detection circuits 107 are formed, and pixels, each including cells that each include a detection electrode 105, are further formed on these detection circuits.

The first substrate 401 includes a number of wirings penetrating the substrate, the number corresponding to a pixel count multiplied by N. An output terminal of a detection circuit provided for each group (P×N detection circuits in the entire CMUT) is connected to a corresponding electrode 407 on another side via the corresponding penetrating wiring. On a second substrate 402, a number of addition circuits, the number corresponding to the pixel count P, are formed.

The electrodes 407 on the first substrate 401 and input terminals 405 of the addition circuits formed on the second substrate 402 are electrically connected by pixel via bumps.

Output signals from the CMUT are drawn out to a plurality of terminals, the number corresponding to the pixel count P, via a number of wirings formed on the second substrate 402, the number corresponding to the pixel count.

By using the CMUT according to the present embodiment, the length of each wiring from the pixels can be minimized, enabling substantial reduction of parasitic capacitances caused by the wirings. Furthermore, the number of penetrating wirings can be reduced compared to that of the fifth embodiment. Accordingly, a sensor with a wider bandwidth, which enables further reduction of a load on the detection circuits, can be provided. In addition, the reliability of the sensor can be enhanced.

Sixth Embodiment

Figure 6:
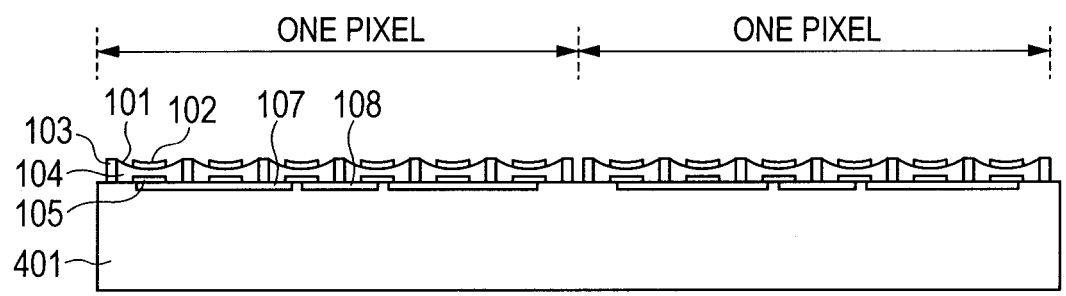
FIG. 6 is a diagram illustrating a capacitive detection type electro-mechanical transducer according to a sixth embodiment.

A CMUT forming a capacitive detection type electro-mechanical transducer according to a sixth embodiment will be described with reference to FIG. 6.

The present embodiment is the same as the first to third embodiments except the positions where detection circuits and addition circuits are formed.

On a substrate 401, N detection circuits 107 and one addition circuit 108 are formed within an area corresponding to one pixel. On these circuits, pixels, each including cells that each include a detection electrode 105, are formed in a two-dimensional array.

Output signals from the CMUT are drawn out to a number of terminals, the number corresponding to a pixel count (P), via a number of wirings formed on the substrate 401, the number corresponding the pixel count.

By using the CMUT according to the present embodiment, the length of each wiring from the pixels can be minimized, enabling substantial reduction of parasitic capacitances caused by the wirings. Accordingly, a sensor with a wider bandwidth, which enables further reduction of a load on the detection circuits, can be provided.

In addition, the length of each wiring between the detection circuits and the addition circuits can be minimized, and thus, signal degradation caused before addition of outputs from the detection circuits can be suppressed, enabling provision of a high-performance CMUT with reduced signal degradation.

Since the configuration of the present embodiment requires arranging a plurality of detection circuits and one addition circuit in each pixel, it is more effective to use the present embodiment in combination of the third embodiment that can suppress the circuit area.

Also, in the third embodiment, current signals are used for transportation from the detection circuits to the addition circuits, and thus, it is highly likely that an increase in length of the wirings may result in noise application and signal degradation, compared to a method using voltages for transportation.

With the present embodiment, the wirings from the detection circuits to the addition circuits can be minimized, and thus, a combination of the present embodiment and the third embodiment enables provision of a high-performance CMUT with further reduced signal degradation.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-003649, filed Jan. 12, 2010, which is hereby incorporated by reference herein in its entirety.

What is claimed is:

1. A capacitive detection type electro-mechanical transducer comprising:
   a plurality of cells, each cell including
   a first electrode and
   a second electrode opposed to the first electrode with a gap between the first and second electrodes, and configured to vibrate;
   a plurality of detection circuits, each detection circuit being configured to detect a current output from a detection electrode that is one of the first and second electrodes; and
   an addition circuit for adding signals from the plurality of detection circuits,
   wherein the plurality of cells are classified into a plurality of groups, each group includes at least two cells,
   wherein a plurality of the detection electrodes of the cells in one group are commonly connected to one detection circuit, and wherein each detection circuit comprises a current amplifying circuit that amplifies currents output from the plurality of detection electrodes of the cells in one group, and wherein the addition circuit comprises a current addition circuit that adds currents output from the plurality of detection circuits, and a current-to-voltage conversion circuit that converts a current output from the addition circuit into a voltage.

2. The capacitive detection type electro-mechanical transducer according to claim 1, further comprising:

a first substrate provided such that the plurality of groups of the cells are arranged on one side of the first substrate, the detection circuits are arranged on the other side of the first substrate opposite to the one side, and a second substrate provided such that the addition circuit is arranged on the second substrate, wherein the detection electrode is connected to an input terminal of the detection circuit through a wiring penetrating the first substrate, and wherein an output terminal of the detection circuit is connected through a bump to an input terminal of the addition circuit.

3. The capacitive detection type electro-mechanical transducer according to claim 1, further comprising:

a first substrate provided such that the detection circuits are arranged on one side of the first substrate, and a second substrate provided such that the addition circuit is arranged on the second substrate, and wherein the plurality of groups of the cells are arranged on the detection circuits corresponding thereto so that the first electrode of the cell is arranged in opposition to the detection circuit, wherein an output terminal of the detection circuit is connected through a wiring penetrating the first substrate to an electrode arranged on the other side of the first substrate opposite to the one side, and wherein an input terminal of the addition circuit is connected through a bump to the electrode arranged on the other side of the first substrate.

4. The capacitive detection type electro-mechanical transducer according to claim 1, further comprising:

a first substrate provided such that the detection circuits and the addition circuit are arranged on one side of the first substrate, wherein the plurality of groups of the cells are arranged two dimensionally on the detection circuits and the addition circuit, and wherein the first electrode of each cell is arranged in opposition to the detection circuit and the addition circuit.

5. The capacitive detection type electro-mechanical transducer according to claim 1, wherein each cell comprises a vibration film on which the second electrode is arranged.

6. The capacitive detection type electro-mechanical transducer according to claim 1, wherein the other electrode of the first and second electrodes is a bias electrode to which a bias voltage is applied.

7. The capacitive detection type electro-mechanical transducer according to claim 1, wherein each cell receives an ultrasonic wave, and wherein an output from the addition circuit corresponds to information of the received ultrasonic wave in one pixel.

* * * * *